United States Patent [19]

Orchard

[11] 4,454,893

[45] Jun. 19, 1984

[54] LOW-NOISE DIAPHRAGM FOR USE IN EXHALATION VALVE

[75] Inventor: Rolf O. Orchard, Manhattan Beach, Calif.

[73] Assignee: Puritan-Bennett Corp., Los Angeles, Calif.

[21] Appl. No.: 326,127

[22] Filed: Nov. 30, 1981

[51] Int. Cl.³ .................... F16K 31/12; F16K 31/145; A61M 16/00
[52] U.S. Cl. .................... 137/494; 251/61.1; 128/205.24
[58] Field of Search ............ 128/205.24, 200.29; 251/61, 61.1, 64, 333; 137/528, 494

[56] References Cited

U.S. PATENT DOCUMENTS 4,190,045  2/1980  Bartels ..................... 128/205.24

Primary Examiner—Kyle L. Howell
Assistant Examiner—Karin Reichle
Attorney, Agent, or Firm—Fulwider, Patton, Rieber, Lee & Utecht

[57] ABSTRACT

A diaphragm (40) for use in an exhalation valve (20) in a respirator. The diaphragm is tapered in thickness to provide substantially reduced vibration and noise. The diaphragm flexes and peels up from its valve seat (32) to provide the improved operation at low flow rates through the valve.

5 Claims, 3 Drawing Figures

LOW-NOISE DIAPHRAGM FOR USE IN EXHALATION VALVE

BACKGROUND OF THE INVENTION

This invention relates generally to flexible diaphragms of the type that serve as flow control valves in respirators or volume ventilators. More particularly, the invention relates to diaphragms for use in exhalation valves of respirators.

A respirator uses a system of tubes to direct a flow of gases to and from a patient. Typically, in a patient breathing circuit there are separate tubes for inhalation and exhalation, the two tubes merging into a common duct near the patient. Valves in the inhalation and exhalation tubes open and close at appropriate times to regulate the breathing cycle. For example, an exhalation valve in the exhalation tube is allowed to open as the patient breathes out, while a check valve simultaneously closes the inhalation tube to prevent flow of exhaled gas into the inhalation tube.

An exhalation valve commonly used in respirators includes a resilient diaphragm mounted in a valve assembly having an inlet port, an outlet port and a control pressure port. In a closed position, the diaphragm rests on a valve seat and covers the inlet port. In the open position, the diaphragm lifts from the valve seat and places the inlet port in fluid communication with the outlet port. The pressure control port admits a control pressure to be applied to the diaphragm from above, and the valve is firmly closed when a relatively large control pressure is applied to the diaphragm. The valve opens when the control pressure is reduced sufficiently to be overcome by expiration pressure supplied by the patient.

This type of valve works satisfactorily for moderate or high flows of exhaled gas, but has a significant drawback at low exhalation flow rates, such as are encountered at the very end of the exhalation phase of a breathing cycle. The problem is particularly acute when the intention is to close the exhalation valve while there is still a small positive pressure within the patient's lungs. This is accomplished by maintaining a small positive control pressure on the diaphragm during the exhalation phase. As the patient exhales, the pressure on the lower face of the diaphragm becomes gradually less, until it is ultimately exceeded by the control pressure on the upper face of the diaphragm. Then the diaphragm should close and prevent any further exhalation flow.

What happens in practice, however, is that at low flows the diaphragm will close initially, and then open again when the exhalation pressure builds up slightly, then close again and open again in a cyclic pattern. This hunting movement of the diaphragm produces undesirable vibration and noise that can be propagated through the entire patient breathing circuit. Accordingly, there has been a significant need for an exhalation valve which substantially reduces vibration and noise under low exhalation flow conditions. The present invention satisfies this need.

SUMMARY OF THE INVENTION

The present invention resides in a diaphragm for use in an exhalation valve assembly which generates little or no audible noise under conditions of low exhalation flow. The key element in the novel diaphragm structure is a resilient disk having an axial thickness that is tapered from one edge of the disk to the opposite edge. Under low flow conditions, the disk is flexed at a region of minimum thickness, to provide a partially open position that permits low flow without significant oscillation of the entire disk.

Briefly, and in general terms, the diaphragm of the invention includes the tapered disk, a cylindrical band formed integrally with the disk and connected to its periphery, an annular support membrane connected to the top of the band, and an integral mounting ring connected to the annular flange and providing means for securing the diaphragm in the valve assembly. The valve assembly further includes a valve chamber with an inlet port, an outlet port and a control pressure port. The diaphragm in the closed position rests on a valve seat covering the inlet port. When the diaphragm lifts from the valve seat, the inlet port is placed in fluid communication with the outlet port. The control pressure port is in fluid communication with that area of the valve chamber above the diaphragm. Thus, when sufficient control pressure is applied above the diaphragm the valve remains closed.

In accordance with another important aspect of the invention, the control pressure port terminates in a nozzle that depends towards the diaphragm. The nozzle acts to prevent any undesired excessive movement of the diaphragm off its valve seat. Lateral vent holes are provided in the nozzle end to permit the control pressure to communicate with the space above the diaphragm even when the diaphragm might be forced up against the nozzle by a strong exhalation flow.

It will be appreciated from the foregoing that the present invention represents a significant advance over earlier valve assemblies used to regulate exhalation flow in respirators. In particular, the valve of the invention operates satisfactorily under low flow conditions as well as high flow conditions, and allows the respirator to be operated in a positive-end-expiration-pressure (PEEP) mode without significant vibration or noise. Other aspects and advantages of the invention will become apparent from the following more detailed description, taken in conjunction with the accompanying drawings.

DESCRIPTION OF THE PREFERRED EMBODIMENT

Figure 1:
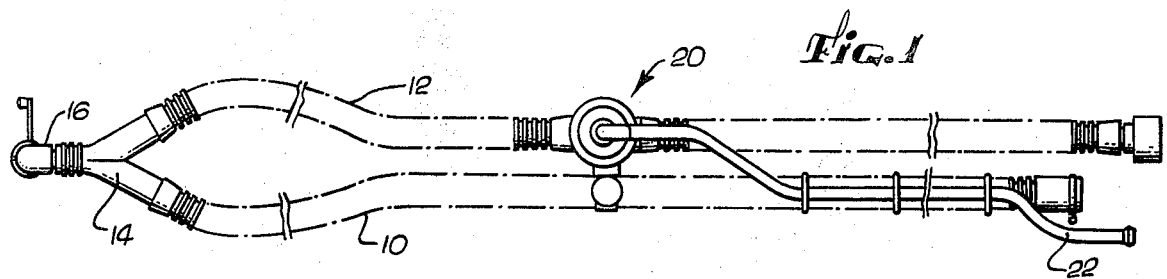
FIG. 1 is a fragmentary schematic view showing a portion of a patient breathing circuit in which the exhalation valve of the invention is used.

As shown in the drawings for purposes of illustration, the present invention is principally concerned with an improved exhalation valve for use in the breathing circuit of a respirator. As shown in FIG. 1, a patient breathing circuit typically includes an inhalation tube, indicated by reference numeral 10, an exhalation tube 12, and a patient wye 14, to which both the inhalation and exhalation tubes are connected. The wye 14 has a third connecting outlet 16, which is coupled to the patient's lungs. An exhalation valve assembly 20 is connected in the exhalation line 12 and is used to control the patient breathing cycle by means of a control pressure line 22 connected to the valve assembly.

Figure 2:
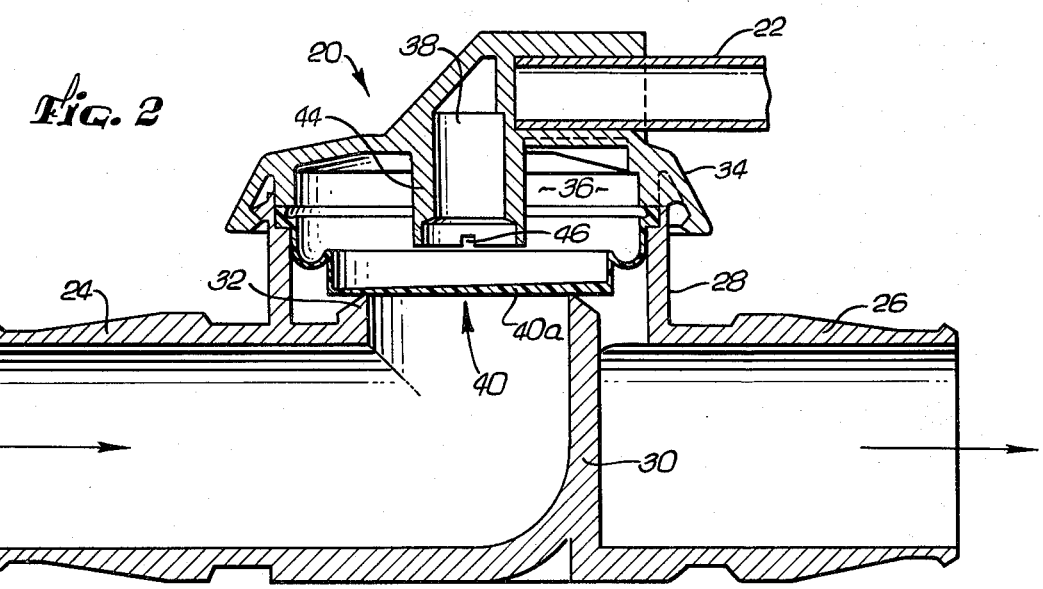
FIG. 2 is an enlarged longitudinal sectional view of the valve assembly of the present invention.

As shown in FIG. 2, the valve assembly 20 includes a cylindrical connector 24 and a cylindrical connector 26, for connection to the exhalation tube 12 (FIG. 1), the two connectors being oriented on a common axis. The valve assembly further includes a cylindrical valve housing 28 of larger diameter than the connectors 24 and 26, and formed integrally with them with its axis perpendicular to the common axis of the connectors. The inlet connector 24 merges inside the housing 28 with a short cylindrical element 30 concentric with the housing and terminating in a valve seat 32 within the housing.

The outlet connector 26 terminates at the wall of the housing 28 and communicates with a volume surrounding the cylindrical element 30. The valve assembly 20 also includes a cover 34 that is fitted in a sealing relationship over the housing 28, to define a valve chamber 36. The control pressure line 22 communicates with the chamber 36 through an opening 38 in the cover 34.

A flexible diaphragm 40 is supported within the housing 28, to engage the valve seat 32. When the control pressure applied to the chamber 36 above the diaphragm exceeds the pressure in the inlet connector 24, the diaphragm 40 is held against the valve seat 32, and exhalation flow is stopped. When the control pressure is removed or sufficiently reduced, the diaphragm is lifted from the valve seat 28 and flow can occur between the inlet and outlet connectors 24 and 26. At low flow rates, the diaphragm tends to vibrate and produce undesirable noise in the breathing circuit.

Figure 3:
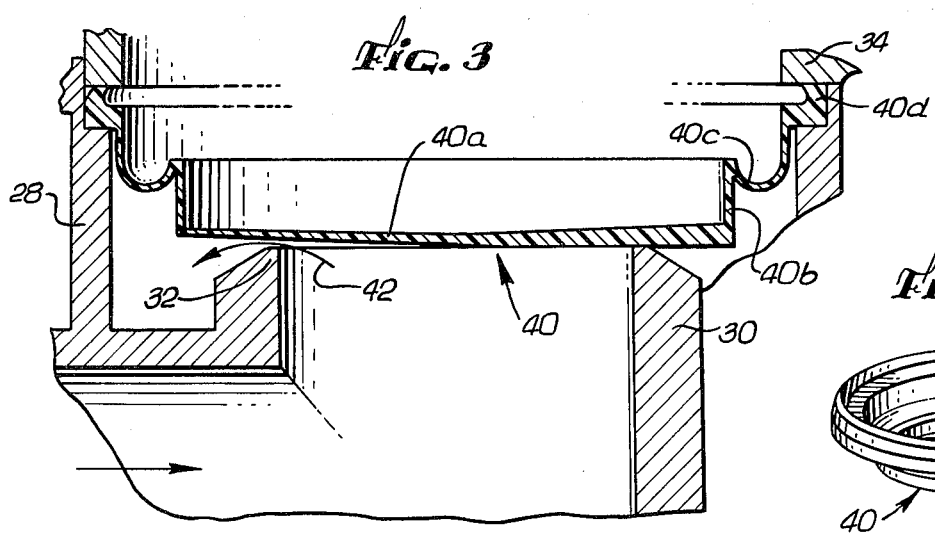
FIG. 3 is a fragmentary and enlarged sectional view of a portion of the valve assembly shown in conditions of low flow.
Figure 4:
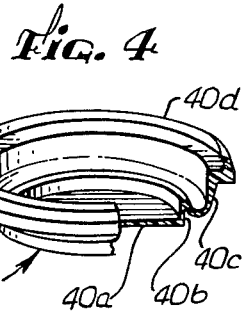
FIG. 4 is a perspective view, partially broken away and in section, of a diaphragm manufactured in accordance with the present invention.

In accordance with the invention, and as best shown in FIG. 3, the diaphragm 40 is tapered in thickness from one edge to an opposite edge, and flexes at a region of thin cross section, to reduce oscillation of the entire diaphragm substantially. The diaphragm 40 includes a central disk, at the edge of which is joined a cylindrical band 40b extending up from the disk. Adjoining the upper edge of the band 40b is an annular suspension membrane 40c, and adjoining the membrane is an annular mounting ring 40d. The mounting ring 40d is secured sealingly between the upper rim of the housing 28 and an edge of the cover 34.

For valve openings at high flow rates, the entire disk 40a lifts from the seat 32 and the support membrane 40c flexes to provide the necessary movement. At low flow rates, however, only a small peripheral region of the disk 40a is peeled up from the seat 28, as shown in FIG. 3, and flow occurs in this small region, as indicated by the arrow 40. Although vibration of the diaphragm 40 is not entirely eliminated, it is substantially reduced, since only a small portion of the diaphragm is subject to oscillation.

In accordance with another important aspect of the invention, the opening 38 through which the control pressure is introduced into the chamber 36, is defined by a tube 44, formed integrally with the cover 34 and extending down toward the diaphragm 40. The tube 44 functions to limit upward movement of the diaphragm 40. If the diaphragm could move without limit, the band 40b could be inverted by a large flow and the diaphragm might not be easily reseated on the valve seat 32.

To prevent the diaphragm from engaging the end of the tube 44 and sealing off flow of control pressure to the valve chamber 36, the tube has a number of openings in it, one of which is indicated at 46, to vent the tube through its sidewall.

It will now be appreciated that the present invention represents a significant advance in the respirator field. In particular, the invention reduces noise and vibration in conditions of low flow through the exhalation valve. Although a specific embodiment of the invention has been described in detail for purposes of illustration, it will be appreciated that various modifications may be made without departing from the spirit and scope of the invention. Accordingly, the invention is not to be limited except as by the appended claims.

I claim:

1. An exhalation valve assembly for controlling exhalation in a respirator, said valve assembly comprising:
    a valve housing defining a closed chamber;
    a diaphragm supported in and extending across said housing and forming a control pressure chamber on one side of said diaphragm and an outlet pressure chamber on the other side of said diaphragm;
    a control pressure passage in fluid communication with said control pressure chamber;
    an outlet passage in fluid communication with said outlet pressure chamber;
    an inlet passage terminating in a valve seat within said outlet pressure chamber and in an operative relationship with said diaphragm, whereby the pressure in said control pressure chamber can be used to control the inlet pressure needed to unseat said diaphragm and place said inlet and outlet passages in fluid communication;
    wherein said diaphragm is tapered in thickness from one edge to another and becomes only partially unseated in low flow conditions, by flexing of said diaphragm at a region of thin cross section.

2. An exhalation valve assembly as set forth in claim 1, wherein said diaphragm includes:
    a central disk of tapered thickness for seating on said valve seat;
    an integral cylindrical band joined by one edge to the circumference of said disk and extending away from said valve seat;
    an annular suspension membrane adjoining and integral with said cylindrical band; and
    an annular mounting ring adjoining and integral with said suspension membrane, for mounting said diaphragm in said valve housing.

3. An exhalation valve assembly as set forth in claim 1 or 2, and further including means for limiting movement of said diaphragm from said valve seat.

4. An exhalation valve assembly as set forth in claim 3, wherein said means for limiting movement of said diaphragm includes a tube defining said control pressure passage and extending into said control pressure chamber.

5. An exhalation valve assembly as set forth in claim 4, wherein said tube has at least one vent in its sidewall to prevent said diaphragm from sealingly closing said tube.

* * * * *